United States Patent
Shin et al.

(10) Patent No.: US 10,723,697 B2
(45) Date of Patent: Jul. 28, 2020

(54) PREPARATION METHOD OF POLYTHIOL FOR OPTICAL LENSES BY USING METAL SULFIDE

(71) Applicant: SKC CO., LTD., Suwon-si, Gyeonggi-do (KR)

(72) Inventors: Junghwan Shin, Suwon-si (KR); Seung Mo Hong, Incheon (KR); Jongmin Shim, Hwaseong-si (KR); Hyuk Hee Han, Suwon-si (KR); Jung Hwan Myung, Seoul (KR); Hyeon Myeong Seo, Ulsan (KR); Yu Jeong Song, Seoul (KR); JooYoung Jung, Pyeongtaek-si (KR)

(73) Assignee: SKC CO., LTD., Suwon-si (KR)

(*) Notice: Subject to any disclaimer, the term of this patent is extended or adjusted under 35 U.S.C. 154(b) by 188 days.

(21) Appl. No.: 15/941,289

(22) Filed: Mar. 30, 2018

(65) Prior Publication Data

US 2018/0282270 A1     Oct. 4, 2018

(30) Foreign Application Priority Data

Mar. 31, 2017 (KR) .................. 10-2017-0041824
Sep. 15, 2017 (KR) .................. 10-2017-0118360

(51) Int. Cl.
| | | |
|---|---|---|
| C07C 319/14 | (2006.01) |
| C07C 319/26 | (2006.01) |
| C08G 18/76 | (2006.01) |
| C08G 18/38 | (2006.01) |
| G02B 1/04 | (2006.01) |
| C08G 18/24 | (2006.01) |
| B29D 11/00 | (2006.01) |

(52) U.S. Cl.
CPC ...... *C07C 319/14* (2013.01); *B29D 11/00009* (2013.01); *C07C 319/26* (2013.01); *C08G 18/246* (2013.01); *C08G 18/3868* (2013.01); *C08G 18/3876* (2013.01); *C08G 18/7642* (2013.01); *G02B 1/041* (2013.01); *G02B 1/043* (2013.01); *B29D 11/00442* (2013.01)

(58) Field of Classification Search
CPC .................. C07C 319/14; C07C 319/26
See application file for complete search history.

(56) References Cited

U.S. PATENT DOCUMENTS

| | | | | |
|---|---|---|---|---|
| 6,100,362 A | * | 8/2000 | Okazaki ............... | C07C 321/14 528/76 |
| 2010/0010192 A1 | | 1/2010 | Kawaguchi et al. | |
| 2010/0029876 A1 | | 2/2010 | Miyata et al. | |
| 2015/0126781 A1 | | 5/2015 | Kawaguchi | |
| 2015/0133692 A1 | | 5/2015 | Kawaguchi et al. | |

FOREIGN PATENT DOCUMENTS

| | | | | |
|---|---|---|---|---|
| CN | 105084324 A | | 11/2015 | |
| EP | 0 665 219 A1 | | 8/1995 | |
| EP | 2 808 321 A1 | | 12/2014 | |
| KR | 1020090031559 A | | 3/2009 | |
| KR | 1020090051090 A | | 5/2009 | |
| KR | 20120058635 A | * | 6/2012 | ........... C07C 319/02 |
| KR | 10-2014-0142375 A | | 12/2014 | |

OTHER PUBLICATIONS

Korean Intellectual Property Office; Communication dated Nov. 9, 2018 in corresponding Application No. 10-2018-0087183.
Hayashi, et al., "High-throughput spectrophotometric assay of reactive oxygen species in serum", Science Direct, Mutation Research 631, 2007, pp. 55-61 (7 pages total).
European Search Report dated Aug. 29, 2018, issued by the European Patent Office for EP 18 16 5086.2.
Korean Intellectual Property Office, Communication dated Jul. 20, 2018, issued in corresponding Korean Application No. 10-2017-0082667.

* cited by examiner

*Primary Examiner* — Rosalynd A Keys
(74) *Attorney, Agent, or Firm* — Sughrue Mion, PLLC

(57) ABSTRACT

Provided is a preparation of a thioether-based polythiol in a high purity using a metal monosulfide for the incorporation of a thioether group, wherein the content of such components as a metal polysulfide present in the metal monosulfide is controlled to a predetermined level or lower. As a result, an optical lens of high quality with a high refractive index can be produced using the polythiol.

15 Claims, No Drawings

US 10,723,697 B2

PREPARATION METHOD OF POLYTHIOL FOR OPTICAL LENSES BY USING METAL SULFIDE

TECHNICAL FIELD

Embodiments relate to a process for preparing a polythiol to which a thioether group is incorporated using a metal sulfide. More specifically, the embodiments relate to a process in which a thioether-based polythiol is prepared in a high purity using a metal sulfide, and an optical lens of high quality with a high refractive index is produced therefrom.

BACKGROUND ART

Plastic optical materials are lightweight, hardly breakable, and excellent in dyeability as compared with optical materials made of inorganic materials such as glass. Therefore, plastic materials are widely used as optical materials for eyeglass lenses, camera lenses, and the like. In recent years, there has been an increased demand for higher performance of optical materials, particularly in terms of high refractive index, high Abbe number, low specific gravity, high heat resistance, high impact resistance, and the like.

The higher the sulfur content in a plastic optical material, the higher the refractive index thereof. Thus, various attempts have been made to add sulfur atoms to the raw material monomers. Due to the binding nature of sulfur atoms, however, it has not been solved to introduce a large number of sulfur atoms in the same molecule.

For this purpose, a polythiourethane-based optical material has been prepared by polymerizing a polythiol containing a thiol group (—SH) at its terminal ends with an isocyanate compound. But it is difficult to contain a sufficient amount of sulfur through the sulfur atoms at the terminal ends only. Thus, a technique of incorporating a thioether group (—C—S—C—) into a molecule has been used together therewith.

In order to incorporate a thioether group into a molecule, a method of reacting a metal monosulfide such as $Na_2S \cdot xH_2O$ (x=5 or 9) with two organic halides has been generally used.

DISCLOSURE OF INVENTION

Technical Problem

The process of synthesizing a thioether-based polythiol for preparing an optical lens with a high refractive index involves numerous steps such as reaction, washing, and the like. Therefore, when a quality problem is found in the final optical lens, it is often difficult to find the step that has caused the problem. For this reason, various conditions that may be problematic at each step have been looked into, and many cases are reported. But there is still room for improvement.

The present inventors have paid attention to the fact that a metal monosulfide used for incorporating a thioether group into a polythiol molecule is susceptible to degradation due to its deliquescence and the like. That is, a metal monosulfide may be contaminated with minor amounts of other components produced during storage or use of metal monosulfide, or these components may be produced during the synthesis of the metal monosulfide. As a result, if this is not taken care of, undesired side reactions may take place during the synthesis of a polythiol, resulting in a deterioration in the purity and color of the polythiol.

These problems can be a serious obstacle to the preparation of a polythiol of uniform quality. In particular, if an optical lens is produced from a polythiol in a low purity, it is difficult to accurately control the refractive index of the optical lens, as well as serious problems may arise in the optical and physical characteristics thereof.

Accordingly, the embodiments described below aim to prepare a thioether-based polythiol in a high purity by controlling a metal monosulfide in advance and putting it into the synthesis reaction of the polythiol and to produce an optical lens of high quality with a high refractive index from the polythiol.

Solution to Problem

According to an embodiment, there is provided a process for preparing a polythiol, which comprises (1) preparing a first composition comprising a metal monosulfide; (2) reducing the content of a metal polysulfide in the first composition to obtain a second composition; (3) reacting the second composition with a halogenated alcohol to synthesize a polyol having a thioether group; and (4) reacting the polyol with thiourea, followed by hydrolysis of the resultant to synthesize a polythiol having a thioether group.

According to another embodiment, there is provided a process for preparing an optical lens, which comprises (1) preparing a first composition comprising a metal monosulfide; (2) reducing the content of a metal polysulfide in the first composition to obtain a second composition; (3) reacting the second composition with a halogenated alcohol to synthesize a polyol having a thioether group; (4) reacting the polyol with thiourea, followed by hydrolysis of the resultant to synthesize a polythiol having a thioether group; and (5) mixing the polythiol with an isocyanate and thermally curing the mixture in a mold.

Advantageous Effects of Invention

According to the embodiments, it is possible to prepare a thioether-based polythiol in a high purity by controlling a metal monosulfide in advance and putting it into the synthesis reaction of the polythiol. As a result, it is possible to produce an optical lens of high quality with a high refractive index from the polythiol.

According to a preferred embodiment, it is possible to effectively prepare a thioether-based polythiol in a high purity by reducing the content of components inclusive of a metal polysulfide contained in a composition comprising a metal monosulfide to a predetermined level or lower and putting the composition into the synthesis reaction of the polythiol.

In addition, through a further embodiment, it is possible to improve the quality of a polythiol in various aspects by suggesting the favorable storage conditions for storage and use of a composition containing a metal monosulfide and exemplifying the conditions for putting the composition into the reaction.

Accordingly, the process for preparing a polythiol according to the embodiments can provide an economical and commercially advantageous way of the quality control of the polythiol.

DETAILED DESCRIPTION FOR CARRYING OUT THE INVENTION

According to an embodiment, the process for preparing a polythiol comprises (1) preparing a first composition comprising a metal monosulfide; (2) reducing the content of a metal polysulfide in the first composition to obtain a second composition; (3) reacting the second composition with a halogenated alcohol to synthesize a polyol having a thioether group; and (4) reacting the polyol with thiourea, followed by hydrolysis of the resultant to synthesize a polythiol having a thioether group.

Hereinafter, each step will be described in detail.

In the above step (1), a first composition comprising a metal monosulfide is prepared.

The first composition can produce a polythiol having a thioether group from two halides by the metal monosulfide, as illustrated in Reaction Scheme 1 below.

[Reaction Scheme 1]

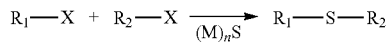

In the above, X is halogen; M is at least one metal element; and n is an integer that varies with the oxidation number of M. For example, X is each fluoro, chloro, bromo, or iodo; M is Na, K, Mn, Ca, or MgBr; and n is 1 or 2 depending on the oxidation number of M.

In addition, in the above, $R_1$ and $R_2$ are each independently a linear or branched C1-C20 alkyl group having at least one hydroxyl group, which may, or may not, contain at least one group selected from the group consisting of —O—, —S—, —C(=O)—O—, —O—C(=O)—O—, —NH—C(=O)—NH—, —NH—C(=S)—O—, —NH—C(=O)—S—, —NH—C(=S)—S—, and —NH—C(=S)—NH— in the alkyl chain.

Such a composition containing a metal monosulfide may be commercially available or may be prepared by a method known in the art.

The first composition mainly comprises a metal monosulfide. For example, the content of the metal monosulfide in the first composition may be 50% by weight or more, 70% by weight or more, or 90% by weight or more.

The metal monosulfide may be represented by the following Formula 1.

$(M)_nS$ [Formula 1]

In the above, M is at least one metal element; and n is an integer that varies with the oxidation number of M. For example, M is Na, K, Mn, Ca, or MgBr; and n is 1 or 2 depending on the oxidation number of M.

The metal monosulfide may be present in the form of a hydrate. For example, in the case of $Na_2S$, it may be present in the form of a hydrate with 5 water molecules ($Na_2S.5H_2O$) or a hydrate with 9 water molecules ($Na_2S.9H_2O$).

As a specific example, the metal monosulfide may be at least one selected from the group consisting of $Na_2S.5H_2O$, $Na_2S.9H_2O$, $K_2S$, MnS, CaS, and $(MgBr)_2S$.

In the course of synthesizing the metal monosulfide, byproducts may be further produced. In addition, since metal monosulfides are deliquescent, they may easily degrade during storage or use thereof. Accordingly, the first composition may further contain other components than the metal monosulfide, which are produced in the course of synthesis, storage, or use thereof.

In general, a metal polysulfide having two or more sulfur atoms is present in the composition comprising a metal monosulfide.

For example, the content of a metal polysulfide in the first composition may be 50% by weight or less, 30% by weight or less, or 10% by weight or less.

As an example, the metal polysulfide may be represented by the following Formula 2.

 [Formula 2]

In the above, M is at least one metal element; n is an integer that varies with the oxidation number of M; and m is an integer of 2 to 8. For example, M is Na, K, Mn, Ca, or MgBr; n is 1 or 2 depending on the oxidation number of M; and m is an integer of 2 to 8.

The metal polysulfide may be present in the form of a hydrate as well.

Specific examples of the metal polysulfide include $Na_2S_2.5H_2O$, $Na_2S_2.9H_2O$, $K_2S_2$, $MnS_2$, $CaS_2$, and $(MgBr)_2S_2$.

In addition, the composition comprising a metal monosulfide may further comprise a small amount of an ammonium salt, a carbonate, a sulfate, an iodide oxide, and the like.

As a specific example, the first composition may comprise a small amount of sodium carbonate ($Na_2CO_3$), sodium sulfate ($Na_2SO_4$), ammonium thiosulfate (($NH_4$)$_2S_2O_3$), trimethylsulfoxonium iodide (($CH_3$)$_3$S(I)O), and the like.

For example, the total content of the ammonium salt, carbonate, sulfate, and iodide oxide in the first composition may be 10% by weight or less or 5% by weight or less.

In the above step (2), the content of a metal polysulfide in the first composition is reduced to obtain a second composition.

It is possible to obtain a second composition having a higher content of a metal monosulfide while the content of a metal polysulfide is reduced by controlling the components contained in the first composition as mentioned above.

Accordingly, the second composition may comprise the metal monosulfide in an amount of 90% by weight or more, 95% by weight or more, 97% by weight or more, or 99% by weight or more. Preferably, the second composition may comprise the metal monosulfide represented by the above Formula 1 in an amount of 95% by weight or more.

In addition, the content of a metal polysulfide in the second composition may be 5% by weight or less. More specifically, the content of a metal polysulfide in the second composition may be 4% by weight or less, 3% by weight or less, 2% by weight or less, or 1% by weight or less. Preferably, the content of a metal polysulfide in the second composition may be 0% by weight or may be a trace amount that slightly exceeds 0% by weight.

Further, since the first composition may contain a small amount of an ammonium salt, a carbonate, a sulfate, and an iodide oxide, the above step (2) may further comprise reducing the content of the ammonium salt, the carbonate, the sulfate, and the iodide oxide in the first composition.

Thus, the total content of the ammonium salt, the carbonate, the sulfate, and the iodide oxide in the second composition may be 5% by weight or less, more specifically, 4% by weight or less, 3% by weight or less, 2% by weight or less, or 1% by weight or less.

In addition, the total content of the metal polysulfide, the ammonium salt, the carbonate, the sulfate, and the iodide oxide in the second composition may be 5% by weight or less, more specifically, 4% by weight or less, 3% by weight or less, 2% by weight or less, or 1% by weight or less.

As a preferred example, the second composition comprises 95% by weight or more of sodium monosulfide ($Na_2S$), and the total content of the sodium polysulfide, the ammonium salt, sodium carbonate, sodium sulfate, and the iodide oxide in the second composition may be 5% by weight or less.

The manner of controlling the components of the first composition in the above step (2) is not particularly limited.

For example, the above step (2) may be carried out by at least one of (a) washing or recrystallizing the first composition using a difference in solubility, and (b) recrystallizing the first composition using a difference in melting point.

The method using a difference in solubility among the above exemplary methods is based on that the metal monosulfide and the other components such as the metal polysulfide in the first composition have different solubilities in water and in an organic solvent (e.g., ethers, alcohols, and the like) with respect to temperature. That is, according to this method, the first composition may be washed several times with water or a mixture of water and an organic solvent to filter an insoluble material or to separate a material precipitated by the difference in solubility with respect to temperature.

Specifically, a metal polysulfide may have a higher solubility than that of a metal monosulfide. Thus, the first composition may be washed with water or a mixture of water and an organic solvent or may be subjected to precipitation by a difference in solubility with respect to temperature, so that it is possible to reduce the content of the metal polysulfide, which has a higher solubility than that of the metal monosulfide, in the composition. Or vice versa.

In addition, the method using a difference in melting point is based on that the metal monosulfide and the other components such as the metal polysulfide in the first composition have melting points different from each other. That is, according to this method, once the first composition has been melted by heating it, a solid material is filtered out, and the remaining liquid material is cooled, followed by sequentially separating recrystallized materials.

The second composition whose components are controlled as described above can be added to the reaction for incorporating a thioether group.

In the above step (3), the second composition prepared in the previous step is reacted with a halogenated alcohol to synthesize a polyol having a thioether group. Here, the halogenated alcohol refers to an alcohol (e.g., a C1-C20 alcohol) substituted with one or more halogens.

As a specific example, in the above step (3), the second composition may be reacted with a chlorodiol to prepare a tetraol having a thioether group. In such event, the chlorodiol may be prepared by reacting an alcohol having a mercapto group with epichlorohydrin.

In such event, the second composition may be put into the reaction after being stored for a certain period of time.

For example, in the above step (3), the reaction with a halogenated alcohol may be carried out after storage of the second composition for one or more days, specifically one day to twelve months, one day to six months, or one day to three months, once the second composition has been prepared in the above step (2).

Here, the storage may be performed under a light-shielding condition at a temperature of 0 to 35° C., at a temperature of 0 to 25° C., or at a temperature of 0 to 20° C.

If the storage temperature exceeds the above range, a metal polysulfide or the like may be generated to cause a side reaction.

If the second composition is solid, it may be put into the reaction in the solid state as it is, or the solid composition may be dissolved in water and then put into the reaction as an aqueous solution.

When the second composition is reacted with a halogenated alcohol, the reaction temperature may excessively rise. In such event, a sulfide may be generated to cause a side reaction. Thus, care must be taken.

Preferably, the reaction with a halogenated alcohol in the above step (3) is carried out by adjusting the amount and the feed rate of the second composition such that the temperature during the reaction is maintained in the range of 0 to 25° C. or 0 to 15° C.

In the above step (4), the polyol obtained in the previous step (3) is reacted with thiourea, followed by hydrolysis of the resultant to synthesize a polythiol having a thioether group.

Specifically, the step (4) comprises (4a) reacting the polyol with thiourea to prepare an isothiouronium salt; and (4b) hydrolyzing the isothiouronium salt under a basic condition to synthesize a polythiol.

In the above step (4a), the polyol may be mixed with thiourea and refluxed under an acidic condition to obtain an isothiouronium salt. In such event, 1 to 3 equivalents, more specifically 1 to 2 equivalents, of thiourea may be reacted per 1 equivalent of the OH group in the polyol. Further, the reflux temperature may be 60 to 130° C., more preferably 90 to 120° C. Also, the reflux time may be 2 to 24 hours, more specifically 6 to 12 hours.

In addition, in the above step (4b), such a basic compound as sodium hydroxide, potassium hydroxide, sodium carbonate, ammonia, or the like may be used for the basic condition. The basic compound may be employed in an amount of 1.0 to 2.5 equivalents, more specifically 1.3 to 1.8 equivalents, per 1 equivalent of the isothiouronium salt. For example, the basic compound may be employed in the form of an aqueous solution. An organic solvent may be added before the basic compound is employed. The amount of the organic solvent added may be 0.1 to 3.0 times, more specifically 0.2 to 2.0 times, the amount of the isothiouronium salt solution. Examples of the organic solvent include toluene, xylene, chlorobenzene, dichlorobenzene, and the like. Toluene is preferred for the purpose of suppressing the formation of byproducts. The reaction temperature for the hydrolysis may be 10 to 130° C., more specifically 30 to 80° C. The time for the hydrolysis may be 0.1 to 6 hours, more specifically 0.5 to 4 hours.

The polythiol thus prepared may be subjected to subsequent steps such as washing, purification, dewatering, and the like.

The polythiol synthesized through the procedures as described above is a bi- or higher-functional polythiol having a thioether group incorporated into the molecule.

For example, the polythiol may have 2 or more, 3 or more, or 4 or more thioether groups in the molecule.

Specifically, the polythiol may have 2 to 10 or 4 to 10 thioether groups in the molecule.

In addition, the polythiol may be a polythiol having 2 to 10, 2 to 8, 2 to 6, or 2 to 4 thiol groups.

Preferably, the polythiol may be a tri-, tetra- or higher-functional polythiol having a thioether group.

As an example, the polythiol may be represented by the following Formula 3.

$$R_1\text{—}S\text{—}R_2 \qquad \text{[Formula 3]}$$

In the above, $R_1$ and $R_2$ are each independently a linear or branched C1-C20 alkyl group substituted with at least one selected from the group consisting of a thiol group, a hydroxyl group, and an amino group, wherein the total number of the entire thiol groups contained in $R_1$ and $R_2$ is 2 to 6; and $R_1$ and $R_2$ may, or may not, each independently contain at least one group selected from the group consisting of —O—, —S—, —C(=O)—O—, —O—C(=O)—O—, —NH—C(=O)—NH—, —NH—C(=S)—O—, —NH—C(=O)—S—, —NH—C(=S)—S—, and —NH—C(=S)—NH— in the alkyl chain.

The polythiol prepared according to the embodiment has a high purity and an excellent color.

For example, the polythiol may have a purity of 70% or more, 75% or more, 80% or more, or 85% or more.

In addition, the polythiol may have a b* value according to the Lab color space of 5 or less, 4 or less, 3 or less, 2 or less, or 1 or less.

Preferably, the polythiol may have a b* value according to the Lab color space of greater than 0 and 2 or less.

According to an embodiment, there is provided a process for producing an optical lens using the polythiol prepared as described above.

That is, the process for preparing an optical lens according to the embodiment comprises (1) preparing a first composition comprising a metal monosulfide; (2) reducing the content of a metal polysulfide in the first composition to obtain a second composition; (3) reacting the second composition with a halogenated alcohol to synthesize a polyol having a thioether group; (4) reacting the polyol with thiourea, followed by hydrolysis of the resultant to synthesize a polythiol having a thioether group; and (5) mixing the polythiol with an isocyanate and thermally curing the mixture in a mold.

The steps (1) to (4) in the process for preparing an optical lens may be carried out according to the conditions and procedures as described above with regard to the steps (1) to (4) of the process for preparing a polythiol. The polythiol prepared as a result is mixed with an isocyanate and thermally cured in a mold.

The isocyanate may be a conventional one commonly used for the synthesis of polythiourethane.

Specifically, it may be at least one selected from the group consisting of an aliphatic isocyanate-based compound such as isophorone diisocyanate, dicyclohexylmethane-4,4-diisocyanate, hexamethylene diisocyanate, 2,2-dimethyl pentane diisocyanate, 2,2,4-trimethylhexane diisocyanate, butene diisocyanate, 1,3-butadiene-1,4-diisocyanate, 2,4,4-trimethylhexamethylene diisocyanate, 1,6,11-undecatriisocyanate, 1,3,6-hexamethylene triisocyanate, 1,8-diisocyanato-4-isocyanatomethyloctane, bis(isocyanatoethyl) carbonate, bis(isocyanatoethyl) ether, 1,2-bis(isocyanatomethyl) cyclohexane, 1,3-bis(isocyanatomethyl) cyclohexane, 1,4-bis(isocyanatomethyl) cyclohexane, dicyclohexylmethane diisocyanate, cyclohexane diisocyanate, methylcyclohexane diisocyanate, dicyclohexyldimethylmethane isocyanate, 2,2-dimethyldicyclohexylmethane isocyanate, bis(isocyanatoethyl) sulfide, bis(isocyanatopropyl) sulfide, bis(isocyanatohexyl) sulfide, bis(isocyanatomethyl) sulfone, bis(isocyanatomethyl) disulfide, bis(isocyanatopropyl) disulfide, bis(isocyanatomethylthio)methane, bis(isocyanatoethylthio)methane, bis(isocyanatoethylthio)ethane, bis(isocyanatomethylthio)ethane, 1,5-diisocyanato-2-isocyanatomethyl-3-thiapentane, 2,5-diisocyanatothiophene, 2,5-bis(isocyanatomethyl)thiophene, 2,5-diisocyanatotetrahydrothiophene, 2,5-bis(isocyanatomethyl)tetrahydrothiophene, 3,4-bis(isocyanatomethyl)tetrahydrothiophene, 2,5-diisocyanato-1,4-dithiane, 2,5-bis(isocyanatomethyl)-1,4-dithiane, 4,5-diisocyanato-1,3-dithiolane, 4,5-bis(isocyanatomethyl)-1,3-dithiolane, 4,5-bis(isocyanatomethyl)-2-methyl-1,3-dithiolane; an aromatic isocyanate compound such as bis(isocyanatoethyl)benzene, bis(isocyanatopropyl)benzene, bis(isocyanatobutyl)benzene, bis(isocyanatomethyl)naphthalene, bis(isocyanatomethyl) diphenyl ether, phenylene diisocyanate, ethylphenylene diisocyanate, isopropylphenylene diisocyanate, dimethylphenylene diisocyanate, diethylphenylene diisocyanate, diisopropylphenylene diisocyanate, trimethylbenzene triisocyanate, benzene triisocyanate, biphenyl diisocyanate, toluene diisocyanate, toluidine diisocyanate, 4,4-diphenylmethane diisocyanate, 3,3-dimethyldiphenylmethane-4,4-diisocyanate, bisbenzyl-4,4-diisocyanate, bis(isocyanatophenyl)ethylene, 3,3-dimethoxybiphenyl-4,4-diisocyanate, hexahydrobenzene diisocyanate, hexahydrodiphenylmethane-4,4-diisocyanate, o-xylylene diisocyanate, m-xylylene diisocyanate, p-xylylene diisocyanate, xylylene diisocyanate, X-xylylene diisocyanate, 1,3-bis(isocyanatomethyl)cyclohexane, diphenyl sulfide-2,4-diisocyanate, diphenyl sulfide-4,4-diisocyanate, 3,3-dimethoxy-4,4-diisocyanatodibenzyl thioether, bis(4-isocyanatomethylbenzene) sulfide, 4,4-methoxybenzenethioethylene glycol-3,3-diisocyanate, diphenyl disulfide-4,4-diisocyanate, 2,2-dimethyldiphenyl disulfide-5,5-diisocyanate, 3,3-dimethyldiphenyl disulfide-5,5-diisocyanate, 3,3-dimethyldiphenyl disulfide-6,6-diisocyanate, 4,4-dimethyldiphenyl disulfide-5,5-diisocyanate, 3,3-dimethoxydiphenyl disulfide-4,4-diisocyanate, 4,4-dimethoxydiphenyl disulfide-3,3-diisocyanate; and a mixture thereof.

More specifically, 1,3-bis(isocyanatomethyl)cyclohexane, hexamethylene diisocyanate, isophorone diisocyanate, xylylene diisocyanate, toluene diisocyanate, or the like may be used as the isocyanate.

First, the polythiol is mixed with an isocyanate to prepare a polymerizable composition. The polymerizable composition may comprise the polythiol and the isocyanate in a mixed state or in a separated state. That is, the polythiol and the isocyanate in the polymerizable composition may be in a state of being compounded in contact with each other or separated from each other so as not to contact each other. The molar ratio of SH group/NCO group in the polymerizable composition may be 0.5 to 3.0, more specifically 0.8 to 1.3.

The polymerizable composition may further comprise such additives as an internal mold release agent, an ultraviolet absorber, a polymerization initiator, a heat stabilizer, a color compensator, a chain extender, a crosslinking agent, a light stabilizer, an antioxidant, a filler, and the like.

The internal release agent may include a fluorine-based nonionic surfactant having a perfluoroalkyl group, a hydroxyalkyl group, or a phosphate ester group; a silicone-based nonionic surfactant having a dimethylpolysiloxane group, a hydroxyalkyl group, or a phosphate ester group; an alkyl quaternary ammonium salt such as trimethylcetylammonium salt, trimethylstearylammonium salt, dimethylethylcetylammonium salt, triethyldodecylammonium salt, trioctylmethylammonium salt, and diethylcyclohexadodecylammonium salt; and an acidic phosphate ester. It may be used alone or in combination of two or more.

As the ultraviolet absorber, benzophenone, benzotriazole, salicylate, cyanoacrylate, oxanilide, or the like may be used.

As the polymerization initiator, an amine-based compound, a phosphorus compound, an organotin compound, an organocopper compound, an organogallium compound, an organozirconium compound, an organoiron compound, an organozinc compound, organoaluminum compound, or the like may be used.

As the heat stabilizer, a metal fatty acid salt, a phosphorus compound, a lead compound, or an organotin compound may be used alone or in combination of two or more.

Thereafter, the polymerizable composition is degassed under reduced pressures and then injected into a mold for molding an optical material. Such degassing and mold injection may be carried out in a temperature range of, for example, 20 to 40° C.

Once the composition is injected into the mold, polymerization is usually carried out by gradually heating the composition from a low temperature to a high temperature. The polymerization temperature may be, for example, 30 to 150° C., more particularly 40 to 130° C. Further, a reaction catalyst, which is conventionally used in the production of polyurethane, may be employed in order to control the reaction rate. As the curing catalyst (or polymerization initiator), a tin-based catalyst may be used. For example, dibutyl tin dichloride, dibutyl tin dilaurate, dimethyl tin dichloride, or the like may be used.

The molded article obtained as a result is released from the mold to thereby obtain a final optical lens.

The optical lens thus prepared is colorless, transparent, and excellent in such optical characteristics as refractive index, Abbe number, and the like.

The optical lens may have a refractive index in the range of 1.56 to 1.78, more specifically in the range of 1.58 to 1.76, in the range of 1.60 to 1.78, in the range of 1.60 to 1.76, in the range of 1.65 to 1.75, or in the range of 1.69 to 1.75.

The optical lens may have an Abbe number of 20 or more, more specifically 30 or more. For example, the Abbe number of the optical lens may be in the range of 20 to 50, in the range of 25 to 50, in the range of 30 to 45, or in the range of 30 to 43.

The optical lens may have a light transmittance, for example, a light transmittance at a wavelength of 550 nm of 85.0% to 99.9%, more specifically 87.0% to 99.0% or 87.0% to 95.0%.

The optical lens may have a yellow index (YI) of 25 or less or 20 or less, specifically in the range of 1 to 25, in the range of 1 to 20, in the range of 3 to 20, or in the range of 5 to 15.

The optical lens may have a glass transition temperature (Tg) of 70° C. or more, 80° C. or more, or 90° C. or more, specifically in the range of 70 to 130° C., in the range of 80 to 125° C., in the range of 90 to 120° C., or in the range of 95 to 115° C.

According to a preferred example, the optical lens may have a glass transition temperature (Tg) of 80 to 125° C. and a yellow index (YI) of 5 to 15.

Further, in such event, the optical lens may have a light transmittance at a wavelength of 550 nm of 85 to 99% and an Abbe number of 30 to 45.

EXAMPLE

Hereinafter, the detailed examples are presented. However, since the detailed constitution of the examples can be modified, the scope of the examples is not limited to those presented below.

Preparation Example 1

Preparation of a Polythiol

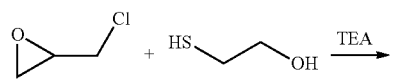

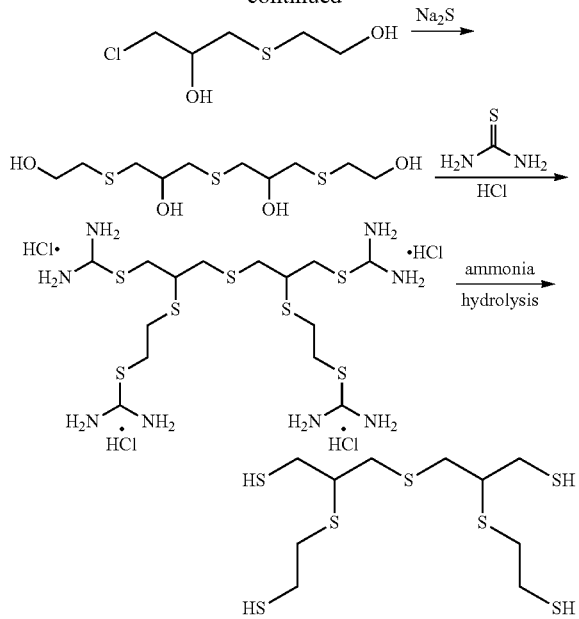

A reactor was charged with a mixture of 78.10 g (2 moles) of 2-mercaptoethanol and 2.0 g of triethylamine. While the mixture was maintained at 35 to 45° C., 92.5 g (1 mole) of epichlorohydrin was added thereto dropwise for 1 hours, followed by the reaction thereof for 1 hour at 40° C. An aqueous solution of a metal sulfide composition was slowly added dropwise to the reactor, and the reaction was carried out at 45° C. for 1 hour. 303.8 g (3.3 moles) of hydrochloric acid (36%) and 190.3 g (2.5 moles) of thiourea were added to the reaction resultant. While the reaction mixture was stirred, it was heated at 110° C. for 9 hours. After the reaction mixture was cooled to room temperature, 400 mL of toluene was added thereto, and 306.5 g (4.5 moles) of aqueous ammonia (25%) was slowly added thereto for the hydrolysis. The organic layer thus obtained was washed twice with 36% hydrochloric acid, 100 mL of water, 100 mL of diluted ammonia, and 100 mL of water. The solvent was removed with a rotary evaporator, and the filtrate was separated by suction filter paper to obtain a polythiol.

Comparative Examples 1 to 5

Preparation of a Polythiol Using an Untreated Metal Sulfide

A polythiol was each prepared according to the procedures of Preparation Example 1 using $Na_2S \cdot 9H_2O$, $K_2S$, MnS, CaS, or $(MgBr)_2S$, which had not been treated.

Example 1

Preparation of a Polythiol Using $Na_2S \cdot 9H_2O$ having Controlled Components Based on a Difference in Solubility A container was charged with 500 g of a composition containing $Na_2S \cdot 9H_2O$ as a main component. 500 mL of a mixture of water and methanol at a ratio of 7:3 was added thereto at 20° C. or lower, followed by vigorous stirring thereof. Thereafter, the composition was washed with a filter to remove the metal polysulfide ($Na_2S_2$) or the like present in the composition. The above procedure was repeated 5 times, and the components in the composition were analyzed. If the composition did not reach the target, the procedure was further repeated 2 to 3 times.

The composition obtained as a result, the components of which had been controlled (i.e., 95% by weight or more of $Na_2S.9H_2O$), was used for the preparation of a polythiol according to the procedures of Preparation Example 1. Here, the composition, the components of which were controlled, was mixed with water at a weight ratio of 1:2 and stirred at 50° C. for 1 hour or longer to sufficiently dissolve the composition. The aqueous solution thus obtained was slowly added dropwise to the reactor. In addition, the amount and the feed rate were controlled during the feeding of the aqueous solution such that the temperature inside the reactor was maintained at 10° C. and that the maximum temperature did not exceed 15° C.

Example 2

Preparation of a Polythiol Using $K_2S$ having Controlled Components Based on a Difference in Solubility A composition containing $K_2S$ as a main component whose components had been controlled in the same manner as in Example 1 was used for the preparation of a polythiol according to the procedures of Preparation Example 1.

Example 3

Preparation of a Polythiol Using MnS having Controlled Components Based on a Difference in Solubility A composition containing MnS as a main component whose components had been controlled in the same manner as in Example 1 was used for the preparation of a polythiol according to the procedures of Preparation Example 1.

Example 4

Preparation of a Polythiol Using CaS having Controlled Components Based on a Difference in Solubility A composition containing CaS as a main component whose components had been controlled in the same manner as in Example 1 was used for the preparation of a polythiol according to the procedures of Preparation Example 1.

Example 5

Preparation of a Polythiol Using $(MgBr)_2S$ having Controlled Components Based on a Difference in Solubility A composition containing $(MgBr)_2S$ as a main component whose components had been controlled in the same manner as in Example 1 was used for the preparation of a polythiol according to the procedures of Preparation Example 1.

Example 6

Preparation of a Polythiol Using $Na_2S.9H_2O$ having Controlled Components Based on a Difference in Melting Point A container was charged with 500 g of a composition containing $Na_2S.9H_2O$ as a main component. The temperature was raised to 120° C. to sufficiently melt the composition. The material precipitated as a solid was filtered out with a filter. Subsequently, while the temperature of the liquid composition was gradually lowered to 60° C., the material precipitated as a solid was filtered out once again with a filter. The temperature of the composition was lowered to 50° C., which is the melting point of $Na_2S.9H_2O$, for rapid solidification, followed by further lowering the temperature to 20° C. The material that was still present as a liquid was removed to obtain a composition whose components had been controlled (i.e., 95% by weight or more of $Na_2S.9H_2O$). The composition whose components had been controlled was used for the preparation of a polythiol according to the procedures of Preparation Example 1.

Preparation Example 2

Preparation of an Optical Lens 481.5 g of the polythiol prepared in Preparation Example 1 above was uniformly mixed with 503.5 g of xylylene diisocyanate, 0.15 g of dibutyltin dichloride as a curing catalyst, and 0.80 g of Zelec® UN of Stepan Company, to thereby prepare a polymerizable composition.

The polymerizable composition was degassed by stirring it under reduced pressures for 30 minutes in a nitrogen atmosphere at room temperature and then filtered through a Teflon filter of 3 μm.

The filtered polymerizable composition was injected using nitrogen pressure into a glass mold assembled by tapes. The glass mold containing the polymerizable composition was heated from 25° C. to 120° C. at a rate of 5° C./min in a forced circulation oven, and polymerization was carried out at 120° C. for 18 hours. The cured resin was further cured at 130° C. for 4 hours, and then the lens was released from the glass mold. The optical lens thus obtained had a center thickness of about 1.2 mm.

Test Methods

The polythiols and the optical lenses prepared above were tested in the following manner.

(1) Analysis of the Components in a Metal Sulfide Composition (% by Weight)

The content of the metal monosulfide in each of the metal sulfide compositions used in the Comparative Examples and the Examples was analyzed by the iodine method. Specifically, 0.2 mL of a 1% aqueous solution of starch was added to 25 mL of a 1% aqueous solution of the composition, and the mixture was sufficiently stirred. Then, a small amount of a 0.1 N (0.05 M) iodine solution was added to the mixture to observe the change in color, and the point at which the color was changed to light purple was taken as the end point. Here, the content (% by weight) of the metal monosulfide in the metal sulfide composition was determined by measuring the amount of the iodine solution used in the titration, the weight of the composition, the amount of the iodine solution required for blank titration, and the like.

(2) Purity of a Polythiol (%)

Since the byproducts generated from the metal polysulfides, ammonium salts, carbonates, sulfates, iodide oxides, and the like have different molecular weights, the polythiol sample was subjected to gel permeation chromatography (GPC). The purity of the polythiol was measured by excluding the components that had a shorter or longer elution time than that of the polythiol as a main component.

(3) Color of a Polythiol (b*)

The color of the polythiol sample was measured using a UV-Vis spectrophotometer (Lambda-365, PerkinElmer).

Specifically, the color was measured at intervals of 1 nm in a wavelength range of 380 to 780 nm using a quartz cell (10 mm×10 mm) and a light source of D65/10°.

(4) Viscosity of a Polythiol (cP)

The viscosity of the polythiol sample was measured using a viscometer (DV3T, Brookfield) under the conditions of CP-51 (cone type) and 10.0 rpm.

(5) Refractive Index and Abbe Number

The refractive index and the Abbe number of the optical lenses were measured at 20° C. using an Abbe refractometer DR-M4 (Atago Co.).

(6) Yellow Index

The optical lenses were measured for chromaticity coordinates x and y using a spectrophotometer (Colormate, Scinco), from which their yellow indices were calculated with Equation 1 below.

$$YI = (234x + 106y + 106)/y \qquad \text{[Equation 1]}$$

(7) Glass Transition Temperature (Tg)

The optical lenses were measured for the glass transition temperature (Tg) with a thermal mechanical analyzer (TMA Q400, TA Instruments Co.) by a penetration method (load of 50 g, pin line of 0.5 mm Φ, temperature elevation rate of 10° C./min).

(8) Stria 100 optical lenses were observed under a mercury lamp with the naked eyes. The lenses having a nonuniform image were classified as having a stria, and the percentage thereof was calculated. As a result, if the percentage of the stria occurrence was less than 5%, it was evaluated as good, and if the percentage of the stria occurrence was 5% or more, it was evaluated as poor.

Test Example 1

Evaluation of a Polythiol According to the Components Control of a Metal Sulfide Composition The components in the metal sulfide compositions used in Comparative Examples 1 to 5 and Examples 1 to 5 were analyzed and are summarized in Table 1 below.

In addition, the purity and the color of the polythiols prepared in Comparative Examples 1 to 5 and Examples 1 to 5 were analyzed and are shown in Table 1 below.

TABLE 1

| | Metal sulfide composition | | Polythiol | |
| | Type of metal monosulfide | Content of metal monosulfide (% by weight) | Purity (%) | Color (b*) |
| --- | --- | --- | --- | --- |
| C. Ex. 1 | $Na_2S \cdot 9H_2O$ | 93 | 62 | 2.7 |
| C. Ex. 2 | $K_2S$ | 93 | 70 | 3.0 |
| C. Ex. 3 | MnS | 90 | 65 | 2.8 |
| C. Ex. 4 | CaS | 94 | 66 | 3.3 |
| C. Ex. 5 | $(MgBr)_2S$ | 94 | 67 | 3.0 |
| Ex. 1 | $Na_2S \cdot 9H_2O$ | 99 | 83 | 0.4 |
| Ex. 2 | $K_2S$ | 98 | 80 | 0.5 |
| Ex. 3 | MnS | 99 | 81 | 0.4 |
| Ex. 4 | CaS | 98 | 79 | 0.7 |
| Ex. 5 | $(MgBr)_2S$ | 99 | 81 | 0.7 |

As shown in Table 1 above, the purity and the color of the polythiols prepared in Examples 1 to 5, in which the components of the metal sulfide compositions had been controlled based on a difference in solubility or in melting point, was significantly improved, as compared with those prepared in Comparative Examples 1 to 5 in which the metal sulfide compositions were used without such treatment.

Test Example 2

Evaluation of an Optical Lens According to the Components Control of a Metal Sulfide Composition An optical lens was prepared according to the procedures of Preparation Example 2 using the polythiols prepared in Comparative Example 1 and Example 1.

The optical lenses prepared as a result were evaluated for the stria, glass transition temperature (Tg), and yellow index (YI). The results are summarized in Table 2 below.

TABLE 2

| | Metal sulfide composition | | Optical lens | | |
| | Type of metal monosulfide | Content of metal monosulfide (% by weight) | Stria | Tg (° C.) | YI |
| --- | --- | --- | --- | --- | --- |
| C. Ex. 1 | $Na_2S \cdot 9H_2O$ | 93 | Poor | 85 | 35 |
| Ex. 1 | $Na_2S \cdot 9H_2O$ | 99 | Good | 107 | 9 |

As shown in Table 2 above, the final optical lens prepared in Example 1, in which the components of the metal sulfide composition had been controlled based on a difference in solubility or in melting point, was significantly improved in terms of stria, glass transition temperature (Tg), and yellow index (YI), as compared with that prepared in Comparative Example 1 in which the metal sulfide composition was used without such treatment.

Test Example 3

Evaluation of a Polythiol and an Optical Lens According to the Feeding Temperature of a Metal Sulfide Composition Polythiols were produced according to the procedures of Example 1, except that the temperature at which the metal sulfide composition was fed into the reactor was changed to 10° C., 20° C., 30° C., and 40° C. (Examples 1A, 1B, 1C, and 1D). The viscosity, purity, and color thereof were measured and are shown in Table 3 below.

Further, optical lenses were prepared according to the procedures of Preparation Example 2 using the polythiols prepared in Examples 1A to Example 1D. The stria, glass transition temperature (Tg), and yellow index (YI) thereof were measured. The results are summarized in Table 3 below.

TABLE 3

| | Metal sulfide composition | | Polythiol | | | Optical lens | | |
|---|---|---|---|---|---|---|---|---|
| | Type of metal monosulfide | Feeding temp. (° C.) | Viscosity (cP) | Purity (%) | Color (b*) | Stria | Tg (° C.) | YI |
| Ex. 1A | Na$_2$S·9H$_2$O | 10 | 203 | 82 | 0.6 | Good | 103 | 9 |
| Ex. 1B | Na$_2$S·9H$_2$O | 20 | 216 | 73 | 1.6 | Good | 98 | 12 |
| Ex. 1C | Na$_2$S·9H$_2$O | 40 | 280 | 65 | 2.9 | Poor | 87 | 20 |
| Ex. 1D | Na$_2$S·9H$_2$O | 60 | 350 | 49 | 6.7 | Poor | 73 | 29 |

As shown in Table 3 above, when the feeding temperature of the metal sulfide composition was maintained at 10° C., the physical properties of the final optical lens as well as those of the polythiol were the most excellent.

Test Example 4

Evaluation of a Polythiol and an Optical Lens According to the Storage Temperature of a Metal Sulfide Composition Polythiols were produced according to the procedures of Example 1, except that the composition whose components had been controlled were stored for 1 month at a temperature of 10° C., 20° C., 30° C., or 40° C., and then fed to the reactor (Examples 1E, 1F, 1G, and 1H). The viscosity, purity, and color thereof were measured and are shown in Table 4 below.

Further, optical lenses were prepared according to the procedures of Preparation Example 2 using the polythiols prepared in Examples 1E to Example 1H. The stria, glass transition temperature (Tg), and yellow index (YI) thereof were measured. The results are summarized in Table 4 below.

TABLE 4

| | Metal sulfide composition | | Polythiol | | | Optical lens | | |
|---|---|---|---|---|---|---|---|---|
| | Type of metal monosulfide | Storage temp. (° C.) | Viscosity (cP) | Purity (%) | Color (b*) | Stria | Tg (° C.) | YI |
| Ex. 1A | Na$_2$S·9H$_2$O | 20 | 198 | 82 | 0.7 | Good | 101 | 11 |
| Ex. 1B | Na$_2$S·9H$_2$O | 30 | 229 | 74 | 1.9 | Good | 96 | 15 |
| Ex. 1C | Na$_2$S·9H$_2$O | 40 | 269 | 71 | 3.9 | Good | 81 | 23 |
| Ex. 1D | Na$_2$S·9H$_2$O | 50 | 350 | 65 | 5.7 | Poor | 69 | 33 |

As shown in Table 4 above, when the storage temperature of the metal sulfide composition was maintained at 20° C., the physical properties of the final optical lens as well as those of the polythiol were the most excellent.

The invention claimed is:

1. A process for preparing a polythiol, which comprises:
   (1) preparing a first composition comprising a metal monosulfide;
   (2) reducing the content of a metal polysulfide in the first composition to obtain a second composition;
   (3) reacting the second composition with a halogenated alcohol to synthesize a polyol having a thioether group; and
   (4) reacting the polyol with thiourea, followed by hydrolysis of the resultant to synthesize a polythiol having a thioether group.

2. The process for preparing a polythiol of claim 1, wherein the content of the metal polysulfide in the second composition is 5% by weight or less.

3. The process for preparing a polythiol of claim 1, wherein the step (2) further comprises reducing the content of an ammonium salt, a carbonate, a sulfate, and an iodide oxide in the first composition.

4. The process for preparing a polythiol of claim 3, wherein the total content of the metal polysulfide, the ammonium salt, the carbonate, the sulfate, and the iodide oxide in the second composition is 5% by weight or less.

5. The process for preparing a polythiol of claim 1, wherein the step (2) is carried out by at least one of (a) washing or recrystallizing the first composition using a difference in solubility, and (b) recrystallizing the first composition using a difference in melting point.

6. The process for preparing a polythiol of claim 1, wherein the reaction with the halogenated alcohol in the step (3) is carried out by adjusting the amount and the feed rate of the second composition such that the temperature during the reaction is maintained in the range of 0 to 15° C.

7. The process for preparing a polythiol of claim 1, wherein the reaction with the halogenated alcohol in the above step (3) is carried out after storage of the second composition for one day to twelve months once the second composition has been prepared in the step (2), and the storage is performed under a light-shielding condition at a temperature of 0 to 20° C.

8. The process for preparing a polythiol of claim 1, wherein the metal polysulfide is represented by the following Formula 2:

$$(M)_nS_m \qquad \text{Formula 2}$$

wherein M is Na, K, Mn, Ca, or MgBr; n is 1 or 2 depending on the oxidation number of M; and m is an integer of 2 to 8.

9. The process for preparing a polythiol of claim 1, wherein the second composition comprises 95% by weight or more of the metal monosulfide represented by the above Formula 1:

$$(M)_nS \qquad \text{Formula 1}$$

wherein M is Na, K, Mn, Ca, or MgBr; and n is 1 or 2 depending on the oxidation number of M.

10. The process for preparing a polythiol of claim 1, wherein the metal monosulfide is at least one selected from the group consisting of Na$_2$S.5H$_2$O, Na$_2$S.9H$_2$O, K$_2$S, MnS, CaS, and (MgBr)$_2$S.

11. The process for preparing a polythiol of claim 1, wherein the second composition comprises 95% by weight or more of sodium monosulfide (Na$_2$S), and the total content of the sodium polysulfide, an ammonium salt, sodium carbonate, sodium sulfate, and an iodide oxide in the second composition is 5% by weight or less.

12. The process for preparing a polythiol of claim 1, wherein the polythiol is represented by the following Formula 3:

$$R_1\text{—}S\text{—}R_2 \qquad \text{Formula 3}$$

wherein $R_1$ and $R_2$ are each independently a linear or branched C1-C20 alkyl group substituted with at least one selected from the group consisting of a thiol group, a hydroxyl group, and an amino group, wherein the total number of the entire thiol groups contained in $R_1$ and $R_2$ is 2 to 6; and $R_1$ and $R_2$ may, or may not, each independently contain at least one group selected from the group consisting of —O—, —S—, —C(=O)—O—, —O—C(=O)—O—, —NH—C(=O)—NH—, —NH—C(=S)—O—, —NH—C(=O)—S—, —NH—C(=S)—S—, and —NH—C(=S)—NH— in the alkyl chain.

13. The process for preparing a polythiol of claim 1, wherein the polythiol has a b* value according to the Lab color space of greater than 0 and 2 or less.

14. A process for preparing an optical lens, which comprises:
 (1) preparing a first composition comprising a metal monosulfide;
 (2) reducing the content of a metal polysulfide in the first composition to obtain a second composition;
 (3) reacting the second composition with a halogenated alcohol to synthesize a polyol having a thioether group;
 (4) reacting the polyol with thiourea, followed by hydrolysis of the resultant to synthesize a polythiol having a thioether group; and
 (5) mixing the polythiol with an isocyanate and thermally curing the mixture in a mold.

15. The process for preparing an optical lens of claim 14, wherein the optical lens has a glass transition temperature (Tg) of 80 to 125° C. and a yellow index (YI) of 5 to 15.

* * * * *